US010313290B2

(12) United States Patent
Chiu et al.

(10) Patent No.: US 10,313,290 B2
(45) Date of Patent: Jun. 4, 2019

(54) SYSTEM AND METHOD FOR COMMUNICATING ELECTRONIC HEALTH INFORMATION

(71) Applicant: MEDIGRAM, INC., Los Altos, CA (US)

(72) Inventors: Michael Chiu, Mountain View, CA (US); Eric Larkin, Los Gatos, CA (US)

(73) Assignee: MEDIGRAM, INC., Los Altos, CA (US)

( * ) Notice: Subject to any disclaimer, the term of this patent is extended or adjusted under 35 U.S.C. 154(b) by 947 days.

(21) Appl. No.: 14/658,087

(22) Filed: Mar. 13, 2015

(65) Prior Publication Data

US 2015/0261931 A1 Sep. 17, 2015

Related U.S. Application Data

(60) Provisional application No. 61/952,144, filed on Mar. 13, 2014, provisional application No. 61/984,852, (Continued)

(51) Int. Cl.
*G06F 19/00* (2018.01)
*H04L 12/58* (2006.01)
(Continued)

(52) U.S. Cl.
CPC ............. *H04L 51/24* (2013.01); *G06F 19/00* (2013.01); *G16H 10/60* (2018.01); *G16H 80/00* (2018.01);
(Continued)

(58) Field of Classification Search
CPC .................................. H04W 4/12; H04L 51/34
(Continued)

(56) References Cited

U.S. PATENT DOCUMENTS 7,702,524 B1 * 4/2010 Whibbs ............... G06F 19/3425
705/2
2006/0026042 A1 * 2/2006 Awaraji ............... G06F 19/328
705/3
(Continued)

OTHER PUBLICATIONS

Greene, Adam H. "HIPAA Compliance for Clinician Texting" Journal of AHIMA 83, No. 4 (Apr. 2012): 34-36.*

*Primary Examiner* — Mark Holcomb
(74) *Attorney, Agent, or Firm* — Procopio, Cory, Hargreaves & Savitch, LLP; Noel C. Gillespie

(57) ABSTRACT

A messaging platform is configured to impose HIPAA-compliant ownership and access control on conversations between caregivers that can contain at least some protected health information (PHI) or electronic protected health information (EPHI). The messaging platform can support a patient-centered conversation between caregivers who are actively affiliated with at least one covered entity in common. The messaging platform can identify caregivers who are authorized participants in a patient-centered conversation based on active affiliations with at least one covered entity. Moreover, the messaging platform can be configured to restrict participation in and access to a patient-centered conversation owned by a covered entity to caregivers who are actively affiliated with the covered entity. Additionally, the messaging platform can permit a caregiver having a professional conversation initiator privilege to initiate a professional conversation that does not contain PHI or EPHI with another caregiver who is not actively affiliated with the same covered entity.

20 Claims, 11 Drawing Sheets

Related U.S. Application Data filed on Apr. 27, 2014, provisional application No. 61/986,748, filed on Apr. 30, 2014, provisional application No. 62/009,920, filed on Jun. 10, 2014, provisional application No. 62/009,921, filed on Jun. 10, 2014.

(51) Int. Cl.
*H04L 12/18* (2006.01)
*G16H 80/00* (2018.01)
*G16H 10/60* (2018.01)

(52) U.S. Cl.
CPC ...... *H04L 12/1822* (2013.01); *H04L 12/1895* (2013.01); *H04L 51/043* (2013.01); *H04L 51/08* (2013.01); *H04L 51/10* (2013.01); *H04L 51/36* (2013.01); *H04L 51/32* (2013.01)

(58) Field of Classification Search
USPC ........................................................ 705/2–4
See application file for complete search history.

(56) References Cited

U.S. PATENT DOCUMENTS

| | | | |
|---|---|---|---|
| 2007/0258626 A1* | 11/2007 | Reiner | A61B 5/1171 382/115 |
| 2009/0164253 A1* | 6/2009 | Lyshkow | G06F 19/321 705/3 |
| 2009/0307755 A1* | 12/2009 | Dvorak | G06Q 10/10 726/4 |
| 2013/0066654 A1* | 3/2013 | Thomason | G06Q 50/22 705/3 |
| 2013/0117039 A1* | 5/2013 | Washburn | G06Q 50/22 705/2 |
| 2013/0346103 A1* | 12/2013 | Griffin | G06Q 50/24 705/3 |
| 2014/0032223 A1* | 1/2014 | Powe | G06F 19/3456 704/275 |
| 2014/0297308 A1* | 10/2014 | Baruch | G06Q 50/22 705/2 |

* cited by examiner

Intentionally blurry

Intentionally blurry

SYSTEM AND METHOD FOR COMMUNICATING ELECTRONIC HEALTH INFORMATION

RELATED APPLICATIONS

The present application claims priority to U.S. Provisional Patent Application No. 61/952,144 filed Mar. 13, 2014, U.S. Provisional Patent Application No. 61/984,852 filed Apr. 27, 2014, U.S. Provisional Patent Application No. 61/986,748, filed Apr. 30, 2014, U.S. Provisional Patent Application No. 62/009,920 filed Jun. 10, 2014, and U.S. Provisional Patent Application No. 62/009,921 filed Jun. 10, 2014, each of which is incorporated by reference herein in its entirety.

BACKGROUND

Today we are connected by ever more powerful devices with ever increasing communication capabilities. Moreover, more and more physical objects or "things" are embedded with electronics, software, sensors and connectivity to enable them to achieve greater value and service by exchanging data. As the amount of information and data being exchanged by communication and other devices increases, the ability to ensure privacy and security of the information and data is becoming harder and harder. For business and other entities looking to take advantage of modern communication and device capability to gather and use data, the difficulty in ensuring privacy and security of the data can lead to liability. A prime example of this is in the health care arena where patient health information is being gathered and exchanged.

The Health Insurance Portability and Accountability Act (HIPAA) of 1996 imposes specific requirements on the management of Protected Health Information (PHI) and Electronic Protected Health Information (EPHI) by covered entities (e.g., physicians, hospitals, and insurance providers) as well as their business associates. The Act engendered a regulatory framework that includes the HIPAA Security Rule and HIPAA Privacy Rule ("HIPAA Rules"). Specifically, the HIPAA Security Rule mandates the use of specific physical, technical and administrative safeguards in information technology (IT) systems that store or transact with Electronic Protected Health Information (EPHI). Meanwhile, the HIPAA Privacy Rule sets protocols with respect to the correction, disclosure, and notification of PHI and EPHI.

One of the most salient aspects of the HIPAA Rules, and the related acts and regulations is that covered entities are held accountable for the security and management of the PHI and EPHI under their control. In practice, each item of PHI or EPHI is treated as being owned by at least one covered entity. This ownership paradigm avoids ambiguity about liability in the event of a security breach.

In addition to the formal medical records that are traditionally maintained for each patient, healthcare providers also routinely engage in ad hoc communication in order to coordinate and facilitate treatment for individual patients. Ad hoc communication can convey PHI and EPHI, and is therefore subject to the same HIPAA Rules as formal patient records. Nevertheless, healthcare providers must rely on legacy communication technologies (e.g., facsimile, paging, and email) to conduct ad hoc communication. Conventional modes of communication are generally insecure and cannot be readily adapted to comply with HIPAA rules.

SUMMARY

According to various embodiments, there is provided a HIPAA-compliant system and method for communicating electronic health information. In one exemplary embodiment, message data that include at least some EPHI can be composed, transmitted, and/or received on a messaging client (e.g., Medigram smartphone or web application). The exchange of message data over a network is mediated by a messaging platform (e.g., Medigram server(s)) that imposes HIPAA-compliant ownership and access control.

In various embodiments, the messaging client can be installed on a caregiver's mobile communication device (e.g., smartphone, laptop, tablet personal computer (PC)). In some embodiments, message data is transmitted directly between the messaging platform and the messaging client. In other embodiments, the messaging platform and the messaging client can communicate through a compact dedicated device (CDD). In one exemplary embodiment, the CDD can act as an intermediary recipient. As such, the CDD can be configured to receive message data from the messaging platform and then forward the message data to the messaging client. In addition, the CDD can also act as an alert agent. In this capacity, the CDD can be configured to respond to incoming message data by providing one or more alerts to the caregiver.

In various embodiments, a first caregiver can use the messaging client and initiate and conduct a conversation with at least a second caregiver. For example, the first caregiver can exchange message data with the second caregiver. The conversation can be patient-centered and the corresponding message data can include at least some EPHI regarding a specific patient. Alternately, the conversation can be a professional conversation that does not relate to any particular patient.

In various embodiments, the messaging platform can attribute ownership of the conversation to one or more covered entities based on the respective affiliations of the caregivers participating in the conversation. Accordingly, the messaging platform can further associate data corresponding to the conversation with the covered entity. In one exemplary embodiment, data associated with different covered entities can be stored separately.

In various embodiments, the messaging platform can restrict participation in and access to the conversation to those caregivers who are actively affiliated with at least one of the covered entities that own the conversation. Thus, a caregiver can be added to a conversation owned by a covered entity if the caregiver is actively associated with the covered entity. Furthermore, a caregiver participating in a conversation can lose access to the conversation in the event that the affiliation between the caregiver and the covered entity owning the conversation is disabled.

In various embodiments, a single caregiver can be affiliated with multiple covered entities. Accordingly, in one exemplary embodiment, the messaging platform can allow a caregiver to participate in and access conversations owned by a first covered entity and conversations owned by a second covered entity. Meanwhile, the caregiver interacts with a single instance of the messaging client but is able to participate in and access conversations owned by different covered entities.

In various embodiments, the affiliation between a caregiver and a covered entity can be linked with privileges and/or restrictions. For example, as between one particular caregiver and the covered entity that the caregiver is actively affiliated with, the caregiver can have privileges that include, for example, but not limited to, affiliations administrator privilege, professional conversation initiator privilege, patient linking privilege, conversation sharing privilege, and conversation transfer privilege.

In various embodiments, ownership of a conversation can be shared amongst different covered entities. Accordingly, in one exemplary embodiment, the messaging platform allows a first caregiver who is affiliated with a first covered entity and having the requisite conversation sharing privilege to add at least a second caregiver who is affiliated with a second covered entity as a participant in an existing patient-centered conversation. In doing so, the messaging platform can further attribute ownership of the conversation to the second covered entity in addition to the first covered entity.

In various embodiments, ownership of a conversation can be transferred from one covered entity to another covered entity. For example, in one exemplary embodiment, a first caregiver who is associated with a first covered entity and whose association with the first covered entity is linked with a requisite conversation transfer privilege can transfer the ownership of an existing patient-centered conversation from the first covered entity to a second covered entity. In other embodiments, the first caregiver having the requisite conversation transfer privilege can remove as participants from an existing patient-centered conversation all caregivers who are actively affiliated with one or more covered entities. In doing so, the messaging platform can attribute ownership of the conversation to one or more covered entities having actively affiliated caregivers who remain as participants in the conversation.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Various embodiments of the systems and methods disclosed herein provide for communicating electronic health information. In the systems and methods disclosed, users can communicate through a simple, unified solution that not only provides privacy and security, but also helps the users and the organizations they are associated with manage the privacy and security using automated, but flexible tools. Many of the embodiments describe herein are related, e.g., to covered entities that must comply with HIPAA. One challenge for caregivers associated with such entities is the ability to communicate in an easy, convenient fashion, using modern communication technology, while still ensuring that any PHI or EPHI is tracked and maintained in a secure fashion.

The systems and methods described herein allow caregivers affiliated with the same or different covered entities to engage in both patient-centered and professional conversations. In various embodiments, a messaging platform can mediate the exchange of message data between caregivers engaged in conversation. In one exemplary embodiment, the messaging platform manages ownership and access to individual conversations according to HIPAA mandates. Thus, each conversation may be owned by at least one covered entity and may be accessed by caregivers with active affiliations with that covered entity.

After reading this description it will become apparent to one skilled in the art how to implement the systems and methods described herein in various alternative embodiments and alternative applications. However, although various embodiments will be described herein, it is understood that these embodiments are presented by way of example only, and not limitation. As such, this detailed description of various alternative embodiments should not be construed to limit the scope or breadth of appended claims.

Figure 1:
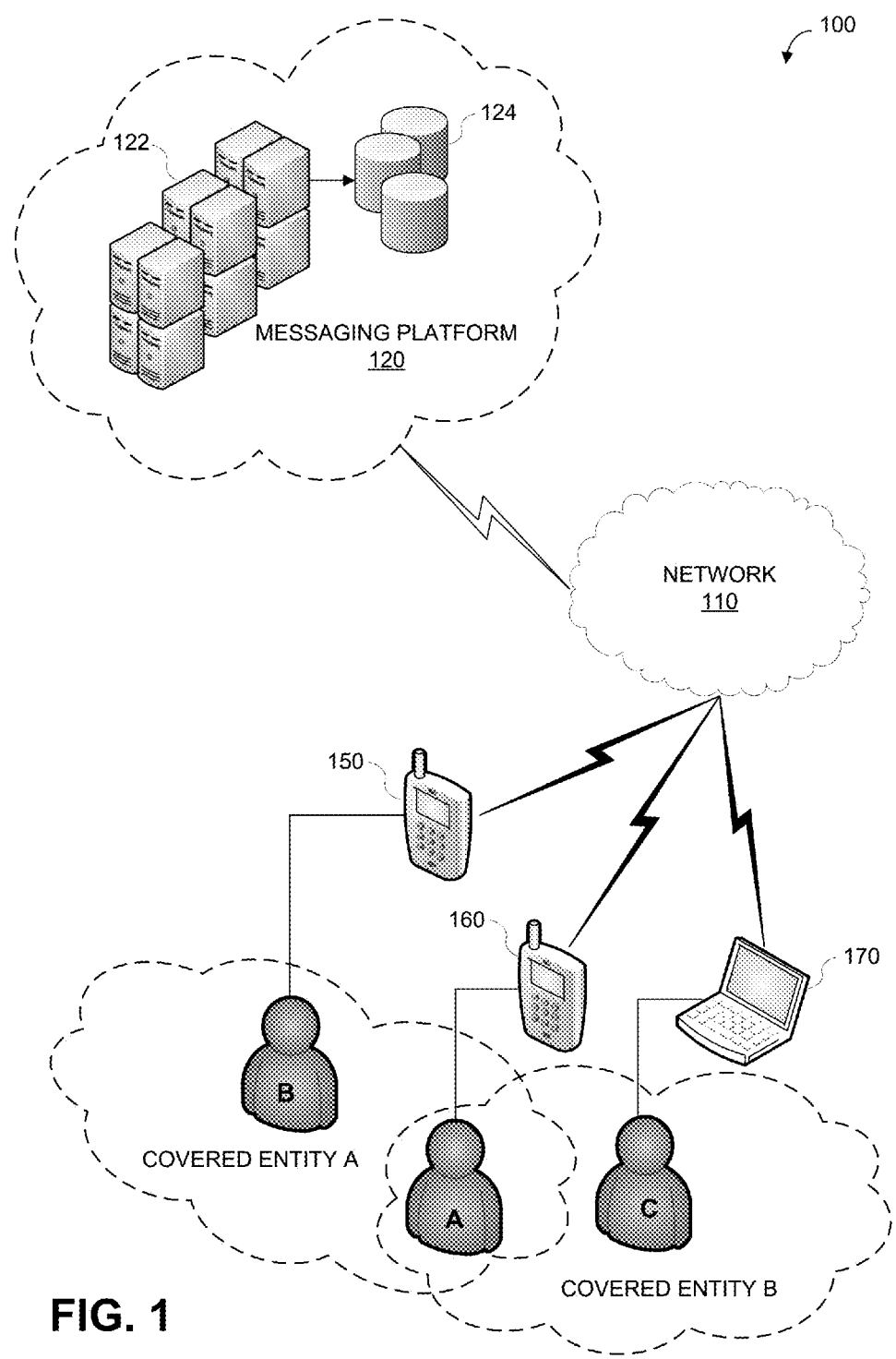
FIG. 1 is a system diagram illustrating a network environment for various embodiments.

FIG. 1 is a system diagram illustrating a network environment 100 configured in accordance with one example embodiment of the systems and methods described herein. Referring to FIG. 1, a messaging platform 120 can include one or more servers 122 and databases 124. In various embodiments, the servers 122 can provide messaging functionalities built on Extensible Messaging and Presence Protocol (XMPP).

According to one exemplary embodiment, the messaging platform 120 is configured to transact (e.g., receive, transmit, store) message data, which can include information that is associated with various privacy and security needs or requirements. For example, the message data can include at least some EPHI that is covered by HIPAA security and privacy mandates. As such, in addition to imposing HIPAA-compliant ownership and access control, as described in more detail below, the messaging platform 120 can also be configured to encrypt at least a portion of the message data stored in the databases 124. Moreover, the messaging platform 120 can be configured to store one or more redundant copies of the message data. For example, the servers 122 and databases 124 can include for example, but not limited to, primary production server(s) and database(s), and standby disaster recovery server(s) and database(s). The primary production database server can be configured to replicate production data in real time to the standby disaster recovery database server, which can be located in a different geographical region.

In various embodiments, the messaging platform 120 can communicate over a network 110 with a plurality of messaging clients, including a first messaging client 150, a second messaging client 160, and a third messaging client 170. The network 110 may be a wired or wireless network.

In the example of FIG. 1, each of the first messaging client 150, the second messaging client 160, and the third messaging client 170 can be installed on a respective mobile communication device (e.g., smartphone, laptop, tablet PC). For example, the first messaging client 150 may be an iOS client using the XMPP Framework while the second messaging client 160 may be an Android client using the Smack XMPP library. Meanwhile, the third messaging client 170 may be a web client. Thus, according to some embodiments, the web messaging client may be a Ruby on Rails application that uses the Ember and Jquery Javascript frameworks with the Strophe.js library for XMPP.

In various embodiments, each of the first messaging client 150, the second messaging client 160, and the third messaging client 170 can be configured to compose, transmit, and receive message data. Moreover, the first messaging client 150, the second messaging client 160, and the third messaging client 170 can store and provide access to a local cache of message data. In at least one exemplary embodiment, the first messaging client 150, the second messaging client 160, and the third messaging client 170 can be configured to encrypt the corresponding local cache of message data.

Referring again to FIG. 1, each of the first messaging client 150, the second messaging client 160, and the third messaging client 170 can be associated with an individual user. In one exemplary embodiment, each messaging client may be associated with a particular caregiver (e.g., physician, nurse). For example, as shown in FIG. 1, the first messaging client 150 is associated with a Caregiver A, the second messaging client 160 is associated with a Caregiver B, and the third messaging client 170 is associated with a Caregiver C.

In various embodiments, each of Caregiver A, Caregiver B, and Caregiver C can be affiliated with one or more covered entities. For example, a physician may be affiliated with one or more hospitals. As shown in FIG. 1, Caregiver A is affiliated with a Covered Entity A and a Covered Entity B. Meanwhile, Caregiver B is affiliated with Covered Entity A and Caregiver C is associated with Covered Entity B. As described in detail below, Caregivers A, B and C can use their devices 150, 160, and 170, respectively, to communicate information with each other that may include PHI. Messaging platform 120 can, however, impose HIPAA-compliant ownership and access control.

As described above, devices 150, 160, and 170 generally comprise standard, or off the shelf communication devices, such as smartphones, tablets, or laptops. In certain instances, the use of such devices may not be possible. For example, often in a hospital setting, such devices cannot be used because of a lack of proper network access or other restrictions. As such, in certain embodiments, a specialized device may be needed to enable the communication of information and data described herein. Such a device is described with respect to FIGS. 2A and 2B.

Compact Dedicated Device (CDD)

Figure 2A:
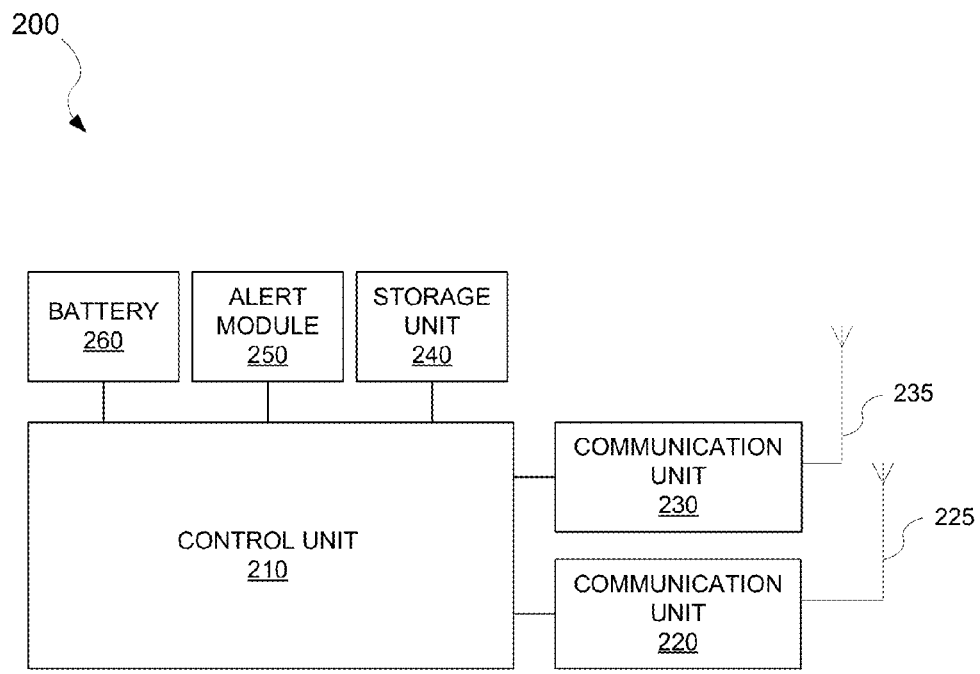
FIG. 2A is a block diagram illustrating a CDD according to various embodiments.
Figure 2B:
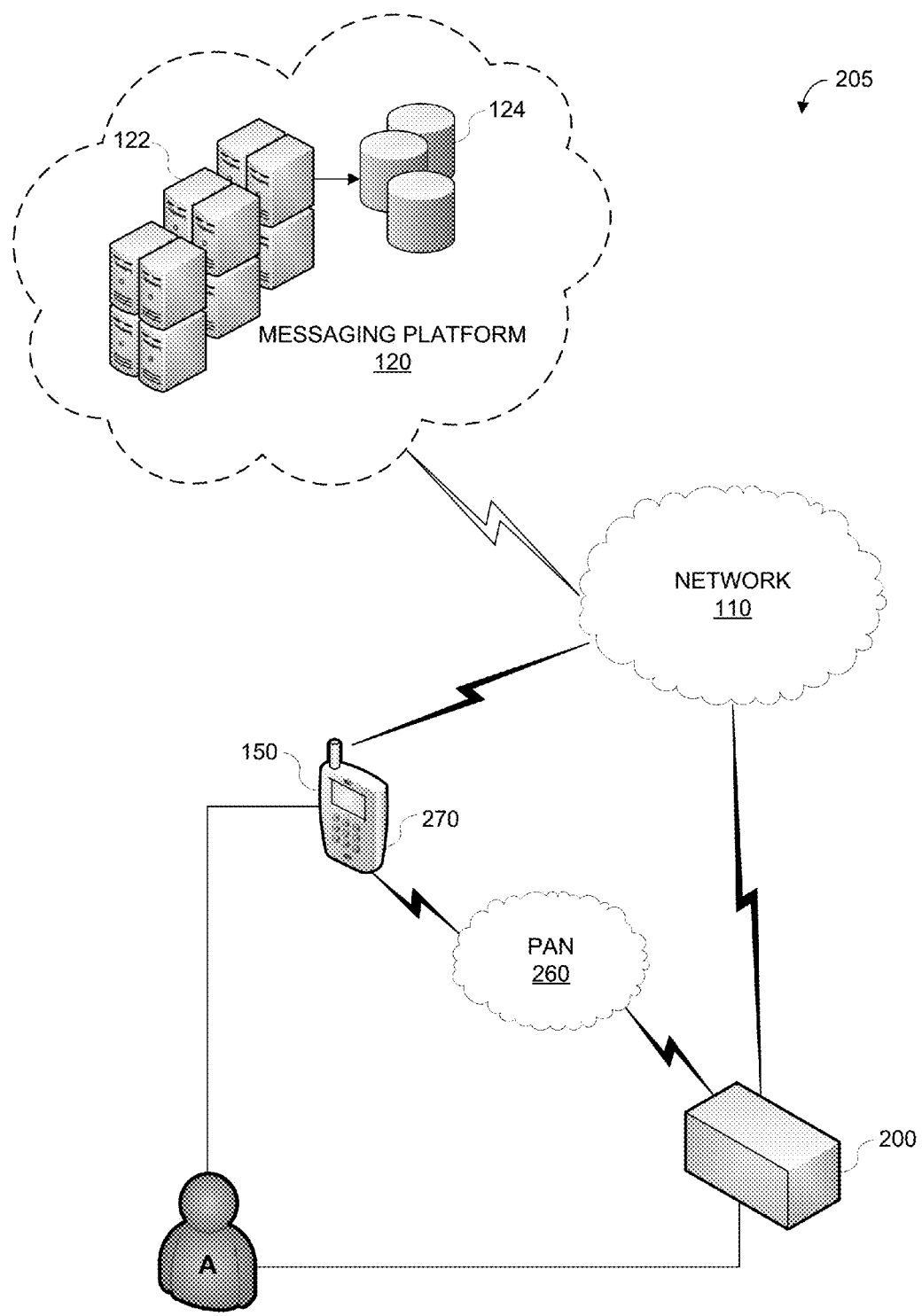
FIG. 2B is a system diagram illustrating a network environment for various embodiments.

FIG. 2A is a block diagram illustrating an CDD 200 according to various embodiments. As shown in FIGS. 2A and 2B, CDD 200 can include a control unit 210, a first communication unit 220, a second communication unit 230, a first antenna 225, a second antenna 235, a storage unit 240, an alert module 250, and a battery 260.

In various embodiments, the CDD 200 can be a device that is capable of long- and short-range wireless communication. Thus, in one exemplary embodiment, the first communication unit 220 can include a radio frequency (RF) chain that is configured to receive message data that is broadcast by the messaging platform 120 via a paging system. Meanwhile, the second communication unit 230 can include a RF chain that is configured to communicate with a mobile communication device via one or more wireless personal area network (PAN) technologies. For example, the CDD 200 can be paired with a mobile communication device using Bluetooth® technology. Alternately or in addition, the CDD 200 can communicate with a mobile communication device via near field communication (NFC). A person having ordinary skill in the art can appreciate that the first communication unit 220 and the second communication unit 230 can be configured to communicate using different wireless technologies as well.

In various embodiments, the control unit 210 can be configured to control the overall operation of the CDD 200 including controlling the functions of the first communication unit 220, the second communication unit 230, the storage unit 240, and the alert module 250. In various embodiments, the control unit 210 can be, for example, but not limited to, a microprocessor or a microcontroller.

In various embodiments, the storage unit 240 can include writable non-volatile memory to store one or more pager identifiers, paring information for a wireless PAN network, and message data received from the messaging platform 120. The storage unit 240 can further include non-volatile program memory. In various embodiments, at least some of the application programs stored at the storage unit 240 can be executed by the control unit 210 for the operation of the CDD 200.

In various embodiments, the alert module 250 can include one or more types of hardware including, for example, but not limited to, a vibrator capable of generating tactile alerts, a speaker capable of generating audible alerts, and a display capable of generating visual alerts (e.g., light-emitting diode (LED)).

In various embodiments, the storage unit 240 can be configured to store application programs, application data, and user data. In various embodiments, at least some of the application programs stored at the storage unit 240 can be executed by the control unit 210 for the operation of the mobile communication device 200.

In various embodiments, the CDD 200 can be powered in full or in part by the battery 260. According to one exemplary embodiment, firmware on the CDD 200 monitors the charge state of the battery 260. In some embodiments, the CDD 200 can be configured to provide an alert using the alert module 250 when the battery 260 approaches a discharged state. The CDD 200 can be further configured to transmit the charge state of the battery 260 to a corresponding messaging client installed on a mobile communication device that is paired with the CDD 200.

Although not shown in FIG. 2A, the CDD 200 can also be powered in full or in part through an audio connector. In one exemplary embodiment, the battery 260 of the CDD 200 can be charged by connecting the CDD 200 via the audio connector to a mobile communication device that is paired or otherwise associated with the CDD 200.

Although not shown in FIG. 2A, according to one exemplary embodiment, the CDD 200 can also be charged using a bulk charging station. The bulk charging station is capable of simultaneously charging multiple CDDs. In various embodiments, connecting the CDD 200 to a bulk charging station can cause firmware on the CDD 200 to wipe at least a portion of the non-volatile memory that is included in the storage unit 240. For example, connecting the CDD 200 to a bulk charging station can cause firmware on the CDD 200 to wipe data including, for example, but not limited to, the pager identifier associated with the CDD 200, paring information for the wireless PAN network, and message data received from the messaging platform 120.

FIG. 2B is a system diagram illustrating a network environment 205 that can support or integrate a CDD 200 in accordance with one example embodiment. Referring to FIGS. 1-2B, the messaging platform 120 can communicate with the CDD 200 instead of directly with a mobile communication device 270 of Caregiver A.

According to one exemplary embodiment, the first messaging client 150 installed on the mobile communication device 270 can be configured to communicate with the CDD 200 over via a PAN 260 using the second communication unit 230. In various embodiments, the CDD 200 is also configured to communicate with the messaging platform 120 over the network 110 using the first communication unit 220.

In some embodiments, the messaging platform 120 can transmit message data to the mobile communication device 270 over the network 110. At the same time, the messaging platform 120 can broadcast, via a paging system, notifications that alerts Caregiver A to the availability of message data. According to one exemplary embodiment, the messaging platform 120, the paging system and the CDD 200 may be configured to implement a general purpose mobile push notification service. Thus, the CDD 200 is configured to receive the notifications but not message data over the paging system from the messaging platform 120. The CDD 200 can be configured to forward the notification to the mobile communication device 270 in response to receiving the notifications from the messaging platform 120. Moreover, the CDD 200 can be configured to generate an alert using the alert module 250. As such, Caregiver A may be made aware of the availability of message data at the mobile communication device 270 but the message data is not transmitted over an insecure paging system to the CDD 200. In some embodiments, the general purpose mobile push notification service is made available to other mobile application or service providers, including zero or more competitive messaging platforms. Thus the messaging platform 120, the paging system and the CDD 200 provide a general purpose mobile push notification service that can alert Caregiver A of the availability of data when mobile communication device 270 is unable to communicate directly over network 110.

In another exemplary embodiment, the CDD 200 can be configured to receive message data from the messaging platform 120 over a paging system or the network 110, and then forward the message data to the first messaging client 150 via the PAN 260.

According to one exemplary embodiment, the CDD 200 is associated with a unique pager identifier. The messaging platform 120 can be configured to store a device list that correlates the pager identifier of the CDD 200 with the mobile communication device 270. Thus, when the messaging platform 120 receives message data that is intended for the mobile communication device 270 of Caregiver A, the messaging platform can use the device list to determine the pager identifier of the CDD 200. In various embodiments, the messaging platform 120 can be configured to broadcast the pager identifier of the CDD 200 along with the message data intended for the mobile communication device 270. Meanwhile, the CDD 200 can determine whether message data is intended for the mobile communication device 270 based on the pager identifier that is transmitted with the message data. The CDD 200 can transmit message data that is intended for the mobile communication device 270 to the mobile communication device 270 using. Alternately, the CDD 200 can disregard and not transmit message data that is not intended for the mobile communication device 270.

In one exemplary embodiment, in response to receiving message data from the messaging platform 120, the CDD 200 can generate an alert using the alert module 250. In various embodiments, the CDD 200 generates alerts based on one or more alert rules. For example, the CDD 200 can be configured to generate an alert if the message data is not successfully forwarded to the first messaging client 150 within a predetermined amount of time. Alternately, the CDD 200 can be configured to always or never generate an alert, regardless of whether the message data received from the messaging platform 120 is successfully forward to the first messaging client 150.

In one exemplary embodiment, the message data that is communicated between the messaging platform 120, the CDD 200, and the first messaging client 150 installed on the mobile communication device 270 is encrypted. For example, the messaging platform 120 can encrypt the message data prior to transmitting the message data to the CDD 200. In various embodiments, the CDD 200 is not provisioned with a key to decrypt the message data. Thus, in various embodiments, the CDD 200 does not decrypt the message data. Instead, the CDD 200 can be configured to forward the still encrypted message data to the first messaging client 150. Meanwhile, in various embodiments, the first messaging client 150 can be provisioned with the key required for decrypting the message data. Thus, in various embodiments, the message data is not decrypted until it is received at the mobile communication device 270. Thus, in various embodiments, loss of the CDD 200 or compromise of the data stored on the CDD 200 does not constitute a breach of EPHI.

Figure 2C:
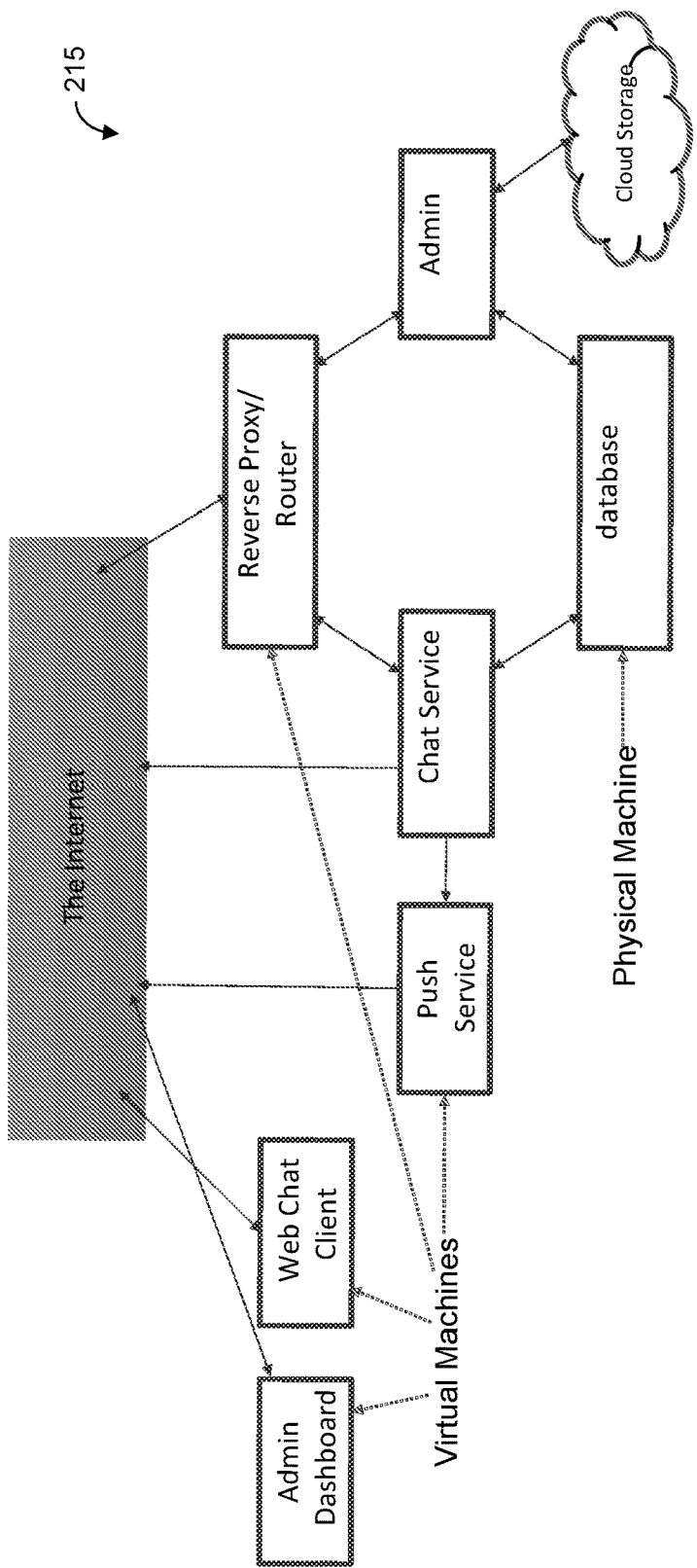
FIG. 2C is a block diagram illustrating production servers according to various embodiments.

FIG. 2C is a block diagram illustrating production servers 215 according to various embodiments. Referring to FIGS. 1 and 2C, in various embodiments, the production servers 215 may implement the servers 122 of the messaging platform 120.

In various embodiments, the messaging platform 120 can be implemented using a hybrid cloud infrastructure that includes virtual cloud servers for applications and services as well as physical servers for database storage.

Figure 2D:
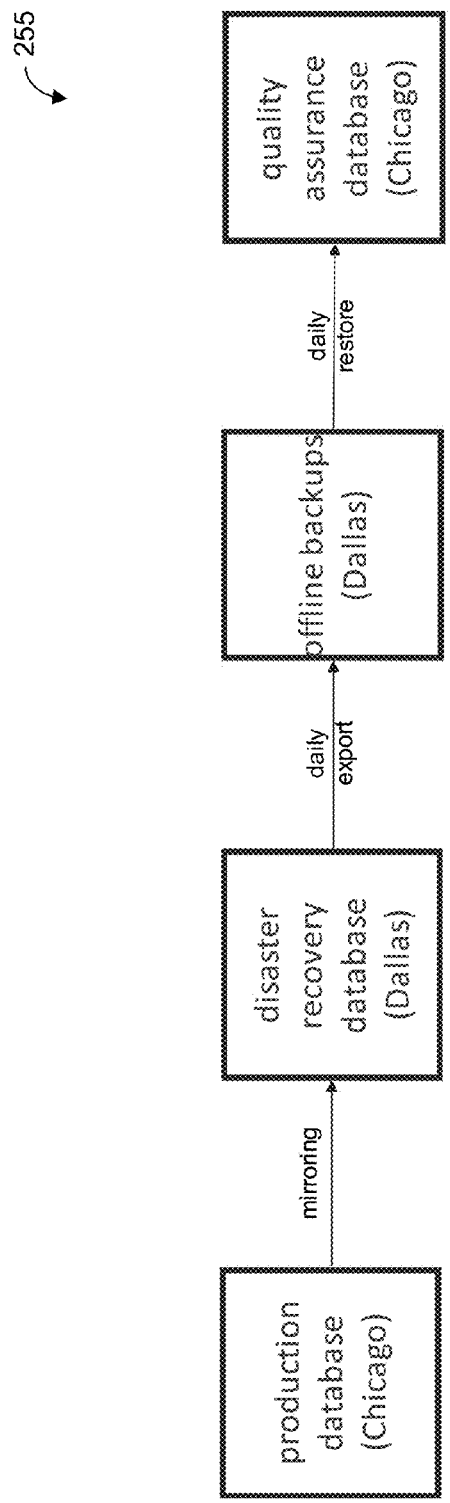
FIG. 2D is a block diagram illustrating production and backup databases according to various embodiments.

FIG. 2D is a block diagram illustrating production and backup databases 255 according to various embodiments. Referring to FIGS. 1 and 2D, in various embodiments, the production and backup databases 255 can implement the databases 124 of the messaging platform 120.

Again referring to FIGS. 1 and 2D, according to one exemplary embodiment, a primary production database can be hosted on a dedicated physical server located in one geographic region (e.g., Chicago, Ill.). In various embodiments, production data is replicated in real time from the primary database server to a standby disaster recovery database located in a different geographical region (e.g., Dallas, Tex.).

In order to restrict access to the EPHI contained in the production and backup databases 255, there can be three instances of the production database. For example, the instances of the production database can include a primary production instance, a warm disaster recovery instance that receives continuous updates from the primary production instances, and a production-test instance used for pre-release quality assurance testing. According to one exemplary embodiment, daily backups are maintained offline on the disaster recovery database server.

HIPAA-Compliant Ownership and Access Control

Recently, the capability of instant messaging and related technologies for use in ad hoc medical communication has been widely recognized. Instant messaging was conceived to facilitate multi-way many-to-many communication, and transparently supports both asynchronous and synchronous communication within the same conversation. These characteristics fit extremely well with the functional requirements for ad hoc medical communication.

In addition, the availability of open source software implementations of instant messaging functionality that rely only on general-purpose TCP/IP networking has made it relatively easy to develop an instant messaging platform that attempts to comply with HIPAA rules. AS a result, a number of new companies are seeking to commercialize HIPAA-compliant instant messaging for ad hoc medical communication. In addition, some companies that provide legacy technologies used in ad hoc medical communication, such as paging technology, have developed HIPAA-compliant messaging products.

These conventional HIPAA-compliant instant messaging solutions are built with a technical architecture in which software clients running on mobile devices or personal computers connect and communicate exclusively with central computers (servers) over a network (client-server architecture).

In conventional HIPAA-compliant instant messaging, the server software typically maintains a list of known end-users as well as a central database that serves as the system of record for all messages and related data (Message Data). The server software runs on one or more central servers that are managed by trusted administrators. Direct access to the central servers and the Message Data stored in the central database is restricted to these trusted administrators. Clients, on the other hand, are typically operated by end-users. The server software accepts connections only from those clients operated by authenticated end-users who are included in its end-user list. Messages entered by end-users on their client device are transmitted to one or more central servers, which in turn relay the message over the network to one or more clients operated by the intended recipients, who are also end-users in the end-user list.

Providers of conventional HIPAA-compliant instant messaging products and services typically generate revenue through subscription or licensing fees charged to Covered Entities such as hospitals and clinics. To make their messaging functionality available to these customers, providers generally use one of two delivery models: either the product is delivered as licensed on-premise software, or as Software-as-a-Service (SaaS). When delivered as on-premise software, the customer typically installs the server software on one or more central computers operated by customer IT staff in a customer-managed datacenter.

When delivered as SaaS, the provider installs and operates the server software on its own computers in a provider-selected datacenter. SaaS offerings may be single-tenant, in which the provider operates multiple instances of the server software, with each instance dedicated to a single customer; however, modem SaaS offerings are typically multitenant, in which the provider hosts data belonging to multiple customers in a single instance of the server software, and relies on an access control system to ensure that each customer maintains control over its own data, and that access to each customer's data is granted only to authorized end-users in compliance with HIPAA rules.

When a conventional HIPAA-compliant instant messaging solution is used as intended, the Message Data created by end-users will frequently contain EPHI, and is therefore subject to HIPAA Rules. To ensure accountability, HIPAA-compliant instant messaging solutions are designed so that each item of Message Data—which may be an item of EPHI—is controlled or "owned" by one and only one customer institution (which is typically a Covered Entity under HIPAA).

In addition to tracking ownership of Message Data, the server software for conventional HIPAA compliant instant messaging must implement an access control system to ensure that access by end-users to the EPHI contained in Message Data complies with the HIPAA Rules. Such end-user access control is implemented by associating each active instance of the client software with a specific user from the end-user list. Typically, the end-user establishes a session on the client by authenticating himself or herself through typical methods (e.g. providing a username and password). Message Data that the authenticated end-user is authorized to access under HIPAA rules is then transmitted by the server software over the network to the end-user's client. In addition, Message Data originating from the client (which may contain EPHI) is then treated by the server software as having been created by the authenticated end-user.

In summary, to ensure compliance all access control systems for HIPAA-compliant instant messaging must perform two actions:

1. Determine and Persist Ownership for New Data: For new Message Data received from a client operated by an authenticated end-user, determine which Covered Entity "owns" or is accountable under HIPAA Rules for the security and management of the new Message Data, and persist the Message Data in the central database in such a way that ownership is tracked.
2. Restrict End-user Access to Existing Data: For each authenticated end-user, restrict Message Data transmitted to the end-user's software client to that subset of Message Data stored in the central database that the end-user is authorized to access under HIPAA Rules.

One conventional method for determining and persisting new data ownership and restricting end-user access to existing data is used when the solution is provided as on premise software or single-tenant SaaS. In the conventional cases, each instance of the server software, with its associated end-user list and central database, are operated by or on behalf of a single Covered Entity. Thus, all end-users on the end-user list and all Message Data in the central database are implicitly associated with the Covered Entity that operates (or on whose behalf the SaaS provider operates) each instance of the server software. The two required actions described in the previous section may be implemented by the following method:

1. Determine and Persist Ownership for New Data: Designate all Message Data originated from a client operated by an authenticated end-user as belonging to the Covered Entity that operates (or on whose behalf the SaaS provider operates) the instance of the server software.
2. Restrict End-user Data Access: Restrict the Message Data transmitted to a software client operated by an authenticated end-user to the subset of Message Data that the end-user previously sent or received.

Another conventional method that is commonly used when the solutions is provided as part of a multi-tenant SaaS implementations of HIPAA-compliant instant messaging is to (a) explicitly associate each end-user account with one and only one Covered Entity, and (b) permit each end-user to send Message Data only to other end-users who are associated with the same Covered Entity. In this case, the two required actions described in the previous section may be implemented by the following method:

1. Determine and Persist Ownership for New Data: Designate all Message Data originated from a client operated by an authenticated end-user as belonging to the Covered Entity with which the end-user's account is affiliated.
2. Restrict End-user Data Access: Restrict the Message Data transmitted to a software client operated by an authenticated end-user to the subset of Message Data that the end-user previously sent or received.

The known methods for access control described above have the common characteristic that each end-user account is either explicitly or implicitly associated with a single Covered Entity. This assumption is problematic for end-users whose work entails creation and access to Message Data owned by more than one Covered Entity. For example, many physicians maintain affiliations with multiple hospitals, and therefore participate in the care of different patients at different hospitals on a daily basis. Typically each hospital is a different Covered Entity. As a result, even if the different hospitals all adopt and use the same multi-tenant SaaS HIPAA-compliant instant messaging solution, under the conventional methods and systems such physicians are unable to access all the Message Data for which they are authorized under HIPAA Rules simultaneously within a single instance of the messaging client. Instead, such physicians must authenticate themselves with one user account in order to create or access Message Data relating to a patient at one hospital, and then must re-authenticate with a different user account in order to create or access Message Data relating to a patient at a different hospital.

But the HIPAA Rules do not require that each end-user account be associated with a single Covered Entity. As such, the embodiments described above and below present systems and methods for determining and persisting new data ownership and restricting end-user access to existing data that is suitable, e.g., for use in a multi-tenant SaaS HIPAA-compliant instant messaging solution in which some or all end-user accounts are associated with more than one Covered Entity.

In one embodiment, some or all end-user accounts in the end-user list are independent of the Covered Entities that own and are accountable for EPHI contained in Message Data. Administrative functionality can be provided to one or more authorized administrators for each Covered Entity that permits the creation or deletion (or enabling and disabling) of an association between the Covered Entity and any end-user account in the end-user list. Such administrative functionality may be provided, for example, through a browser-based web application, access to which is restricted to administrators.

In one embodiment, the ability of each end-user to send and receive messages is restricted such that the end-user may only send messages to a subset of other end-users in the end-user list. The restricted subset consists of other end-users who have active associations with one or more of the Covered Entities with which the end-user has an association. The existence of an active association between an end-user account and a Covered Entity authorizes the end-user who owns the associated end-user account to create and access some of the Message Data owned by the associated Covered Entity. All Message Data created by end-users are grouped into Conversations, and each Conversation is owned by one and only one Covered Entity. A Conversation has one or more participants who are end-users from the end-user list. Participants have an association with one or more Covered Entities in common (the common Covered Entities).

Thus, an end-user may create a new conversation, e.g., using system 100 through the following steps:

1. The first participant in a new Conversation is the end-user who is creating the Conversation (creator). The common Covered Entities at this step is the list of all Covered Entities with which the creator has an active association.
2. Optionally select another participant from the subset of end-users who have active associations with one or more of the common Covered Entities.
3. Repeat step 2 until all desired participants have been selected.
4. If there is still more than one common Covered Entity, select the Covered Entity that will own the newly created Conversation.
5. Create the new Conversation by composing and sending the first message of the new Conversation to the selected participants.

Thus, a participant in an existing Conversation may add another end-user as a new participant only if the other end-user has an active association with the Covered Entity that owns the Conversation. Conversely, a participant is restricted from adding another end-user as a new participant in an existing Conversation if the selected end-user does not have an active association with the Covered Entity that owns the Conversation.

In certain embodiments, any participant may remove himself or herself or any other participant from the participant list of a Conversation. If an administrator deletes or disables the association between a participant and the Covered Entity that owns a Conversation, then the affected participant is removed from the participant list for the Conversation.

Thus, in accordance with the systems and methods described herein, the two required actions for access control in HIPAA-compliant instant messaging solutions are implemented by the following method:

1. Determine and Persist Ownership for New Data: For new Message Data originated from a client operated by an authenticated end-user, designate Message Data as belonging to the Covered Entity that owns the Conversation, determined as described above and below, containing the Message Data.
2. Restrict End-user Data Access: Restrict the Message Data transmitted to a software client operated by an authenticated end-user to the subset of Conversations in which the end-user is a participant.

Thus a system configured as described herein complies with the HIPAA Rules, and maintains the "one owner" design approach to avoid ambiguity about which Covered Entity is legally responsible in the event of a security breach that results in unauthorized access to a particular item of EPHI. In addition, it allows physicians who maintain affiliations with multiple hospitals, and participate in the care of different patients at different hospitals on a daily basis, to access all the Message Data for which they are authorized under HIPAA Rules simultaneously within a single instance of the messaging client.

Figure 3:
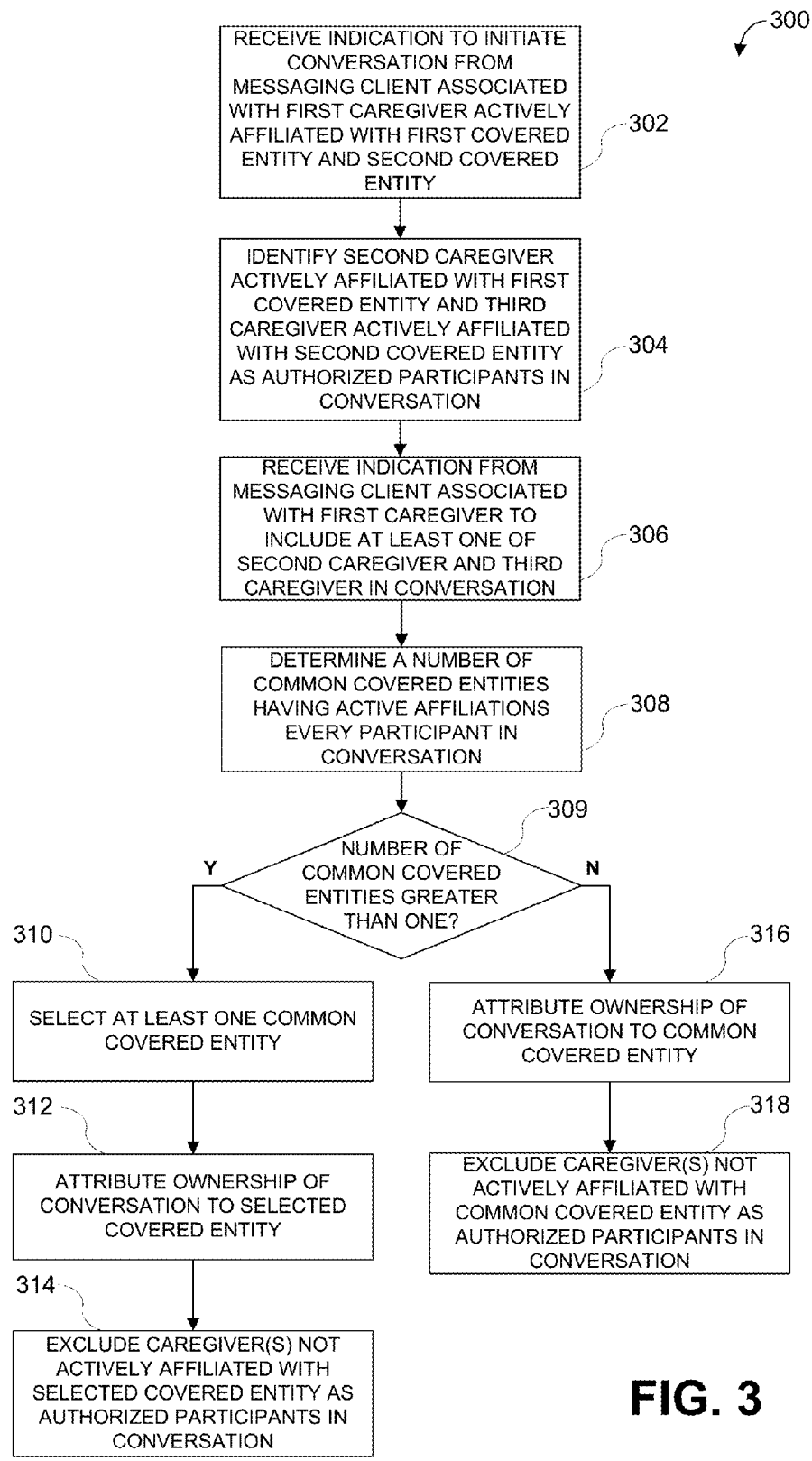
FIG. 3 is a flow diagram illustrating a process for conducting a conversation according to various embodiments.

As noted above, the systems shown in FIGS. 1 and 2B can implement workflow processes that maintain privacy and security for, e.g., ad hoc communications. FIG. 3 is a flow diagram illustrating a process 300 for conducting a conversation according to various embodiments, such as just described. Referring to FIGS. 1 and 3, in various embodiments, the process 300 can be performed by the messaging platform 120.

The messaging platform 120 can be configured to receive an indication initiate a conversation from a messaging client associated with a first caregiver actively affiliated with a first covered entity and a second covered entity (302). For example, Caregiver A can use the first messaging client 150 to start a new conversation. As will be described in more detail below, the conversation can be a patient-centered conversation or a professional conversation that does not relate to a specific patient.

In response to receiving the indication, the messaging platform 120 can be configured to identify a second caregiver actively affiliated with the first covered entity and a third caregiver actively affiliated with the second covered entity as authorized participants in the conversation based on a respective active affiliations of the first caregiver, the second caregiver, and the third caregiver (304). For example, Caregiver A is actively affiliated with Covered Entity A and Covered Entity B. As such, HIPAA mandates permit Caregiver A to conduct conversations (e.g., patient-centered) with both Caregiver B and Caregiver C. The messaging platform 120 can be configured to cause the first messaging client 150 to indicate to Caregiver A that Caregiver B and Caregiver C are authorized participants that may be added to the conversation. A person having ordinary skill in the art can appreciate that the first messaging client 150 can indicate many additional authorized participants based on the active affiliations between various caregivers and at least Covered Entity A and Covered Entity B.

Continuing with the example shown in FIG. 3, the messaging platform 120 can be configured to receive an indication from the first caregiver to include at least one of the second caregiver and the third caregiver in the conversation (306). For example, Caregiver A can add Caregiver B to the conversation since both Caregiver A and Caregiver B are actively affiliated with at least one common covered entity (e.g., Covered Entity A). Alternately, Caregiver A can add Caregiver C to the conversation as both Caregiver A and Caregiver C are actively affiliated with Covered Entity B.

In response to the indication to include at least one of the second caregiver and the third caregiver in the conversation, the messaging platform 120 can be configured to determine a number of common covered entities having active affiliations with every participant in the conversation (308). For example, Caregiver A and Caregiver B can be actively affiliated with a single covered entity (e.g., Covered Entity A). Alternately, Caregiver A and Caregiver B can both be actively affiliated with more than one common covered entity. For instance, Caregiver A and Caregiver B can be affiliated with both Covered Entity A and Covered Entity B.

If the messaging platform 120 determines that the number of common covered entities having active affiliations with every participant in the conversation is greater than one (309—Y), the messaging platform 120 can be configured to select at least one of the common covered entities (310) and attribute ownership of the conversation to the selected covered entity (312). For example, the messaging platform 120 can be configured to select at least one of the common covered entities based on input from one of Caregiver A, Caregiver B, or any other appropriate personnel from Covered Entity A and/or Covered Entity B. Thus, if Caregiver A and Caregiver B are actively associated with both Covered Entity A and Covered Entity B, Caregiver A or Caregiver B can indicate to the messaging platform 120 that ownership of the conversation should be attributed to Covered Entity A and/or Covered Entity B.

Moreover, the messaging platform 120 can associate data corresponding to the conversation with the selected covered entity. As such, a caregiver who is not actively affiliated with the selected covered entity cannot access data corresponding to the conversation.

In addition, the messaging platform 120 can be configured to exclude one or more caregivers not actively affiliated with the selected covered entity as authorized participants in the conversation (314). For example, based on input from Caregiver A and/or Caregiver B, the messaging platform 120 can attribute ownership of the conversation to Covered Entity A. Meanwhile, Caregiver C is not actively affiliated with Covered Entity A. As such, the messaging platform 120 can be configured to exclude Caregiver C as an authorized participant in the conversation owned by Covered Entity A.

Otherwise, if the messaging platform 120 determines that the number of common covered entities having active affiliations with every participant in the conversation is not greater than one (309—N), the messaging platform 120 can be configured to attribute ownership of the conversation to the common covered entity (316). For example, the messaging platform 120 can attribute ownership of the conversation to Covered Entity A since Caregiver A and Caregiver B are both actively affiliated with only Covered Entity A. The messaging platform 120 can associated data corresponding to the conversation with Covered Entity A and prevent caregivers not actively affiliated with Covered Entity A from accessing the data.

Moreover, the messaging platform 120 can be configured to exclude one or more caregivers not actively affiliated with the common covered entity as authorized participants in the conversation (318). For example, Caregiver C is actively affiliated with Covered Entity B but not with Covered Entity A. Thus such, the messaging platform 120 can be configured to exclude Caregiver C as an authorized participant in the conversation owned by Covered Entity A.

In this manner, in various embodiments, the messaging platform 120 can be configured to implement HIPAA-compliant access control to the conversation. Thus, a caregiver can participate in and/or otherwise have access to a conversation if the caregiver has and maintains an active affiliation with at least one of the covered entities owning the conversation. For example, both Caregiver A and Caregiver B can participate in and access a patient-centered conversation owned by Covered Entity A. However, if the affiliation between Caregiver A and Covered Entity A is deactivated, then Caregiver A can no longer participate in or have access to the conversation owned by Covered Entity A.

Now that the conversation has been generated and assigned to a specific covered entity, the message data that is associated with that conversation can be stored, e.g., in the databases 124. For example, the messaging platform 120 can include records associated with and maintained for each of the associated covered entities, in this case Covered Entities A and B. The messages being communicated between, e.g., Caregiver A and Caregiver B can be passed through platform 120 under the control of the corresponding messaging clients (e.g., the first messaging client 150 and the second messaging client 160). In this manner, the messages can be captured and kept as a record associated with the correct covered entity.

In certain embodiments, the records maintained by system 120 can be exported as electronic medical records (EMRs) maintained by a particular covered entity.

Patient-Centered Conversation and Professional Conversation

The messaging platform 120 permits caregivers to engage in different types of conversations. In various embodiments, the messaging platform 120 can be configured to support patient-centered conversations. A patient-centered conversation relates to a specific patient. As will be described in more detail below, a patient can be associated with one or more covered entities (e.g., Covered Entity A and/or Covered Entity B). In one exemplary embodiment, the messaging platform 120 can be configured to restrict ownership of a patient-centered conversation regarding a patient to the one or more covered entities that are associated with the patient.

In various embodiments, the messaging platform 120 can be configured to also support professional conversations. A professional conversation is suitable for non-patient-centered professional communication and can take place between two caregivers who do not have active affiliations with at least one common covered entity. For example, Caregiver B and Caregiver C can engage in a professional conversation via the messaging platform 120. Caregivers engaged in a professional conversation disclose health information that does not meet the criteria for PHI or EPHI. Nevertheless, for reasons of caution and convenience, professional conversations can be conducted via the messaging platform 120 and in accordance with HIPAA mandates.

In various embodiments, the messaging platform 120 can be configured to attribute ownership of a professional conversation to at least one covered entity even though PHI or EPHI would not be disclosed during the professional conversation. As such, the messaging platform 120 maintains accountability in the event that health information disclosed within a professional conversation is later determined to have been improperly disclosed and to meet the legal standard for PHI or EPHI.

In various embodiments, a caregiver can be required to have the requisite privilege with respect to a particular covered entity to initiate a professional conversation (e.g., professional conversation initiator privilege). For example, the affiliation between Caregiver B and Covered Entity A can be linked with a professional conversation initiator privilege. Thus, in order to for Caregiver B who is actively affiliated with Covered Entity A to initiate a professional conversation with Caregiver C who is affiliated with a Covered Entity B, the messaging platform 120 can be configured to determine whether Caregiver B has the requisite professional conversation initiator privilege.

Figure 4:
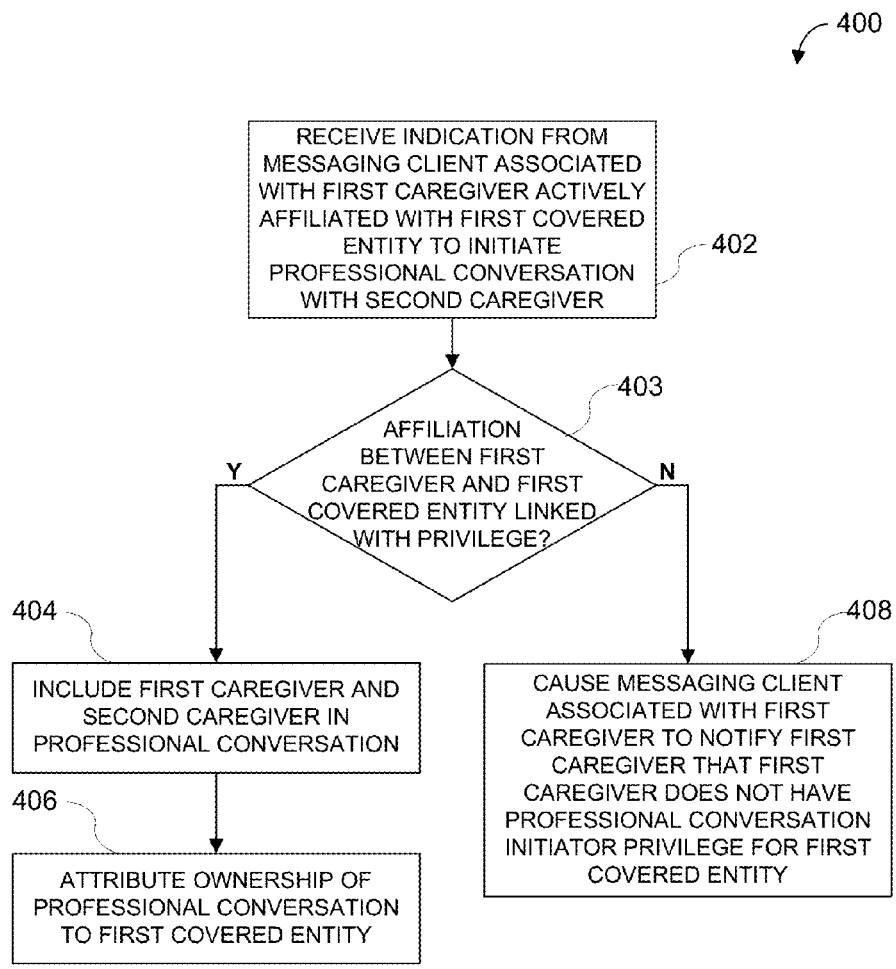
FIG. 4 is a flow diagram illustrating a process for conducting a professional conversation according to various embodiments.

FIG. 4 is a flow diagram illustrating a process 400 for conducting a professional conversation according to various embodiments. Referring to FIGS. 1 and 4, the process 400 can be performed by the messaging platform 120.

In various embodiments, the messaging platform 120 can be configured to receive an indication from a messaging client associated with a first caregiver actively affiliated with a first covered entity to initiate a professional conversation with a second caregiver (402). The first caregiver and the second caregiver can both be actively affiliated with the same first covered entities. For example, Caregiver A can use the first messaging client 150 to initiate a professional conversation with either Caregiver B or Caregiver C. However, the messaging platform 120 can also support professional conversations between caregivers who are not actively affiliated with the same covered entities. For example, Caregiver B can use the second messaging client 160 to initiate a professional conversation with Caregiver C. Using the first messaging client 150, Caregiver A can also initiate a professional conversation that includes both Caregiver B and Caregiver C.

In response to the indication, the messaging platform 120 can determine whether the affiliation between the first caregiver and the first covered entity is linked with a privilege to initiate a professional conversation (403). For example, Caregiver A can have the requisite professional conversation initiator privilege with respect to Covered Entity A, which allows Caregiver A to initiate a professional conversation with caregivers who are and who are not actively affiliated with Covered Entity A.

If the messaging platform 120 determines that the affiliation between the first caregiver and the first covered entity is linked with the privilege to initiate a professional conversation (403—Y), then the messaging platform 120 can be configured to include the first caregiver and the second caregiver as participants in a professional conversation (404). Furthermore, the messaging platform 120 can be configured to attribute ownership of the professional conversation to the first covered entity (406).

On the other hand, the messaging platform 120 can determine that the affiliation between the first caregiver and the first covered entity is not linked with the privilege to initiate a professional conversation (403—N). As such, the messaging platform 120 can cause a messaging client associated with the first caregiver to notify the first caregiver that the first caregiver does not have professional conversation initiator privilege for the first covered entity (408).

HIPAA-Compliant Ownership Sharing

In various embodiments, the messaging platform 120 can be configured to attribute ownership of a conversation to more than one covered entity. In particular, the messaging platform 120 is configured to maintain HIPAA compliance while sharing ownership of a patient-centered conversation amongst multiple covered entities. As such, caregivers actively affiliated with different covered entities are able to participate in and access the same patient-centered conversation.

For example, Caregiver A can have the requisite conversation sharing privilege with respect to Covered Entity A and/or Covered Entity B. Thus, Caregiver A can add Caregiver C to the conversation owned by Covered Entity A even though Caregiver C is actively affiliated with Covered Entity B and not Covered Entity A. In doing so, the messaging platform 120 can attribute ownership of the conversation to both Covered Entity A and Covered Entity B.

Figure 5:
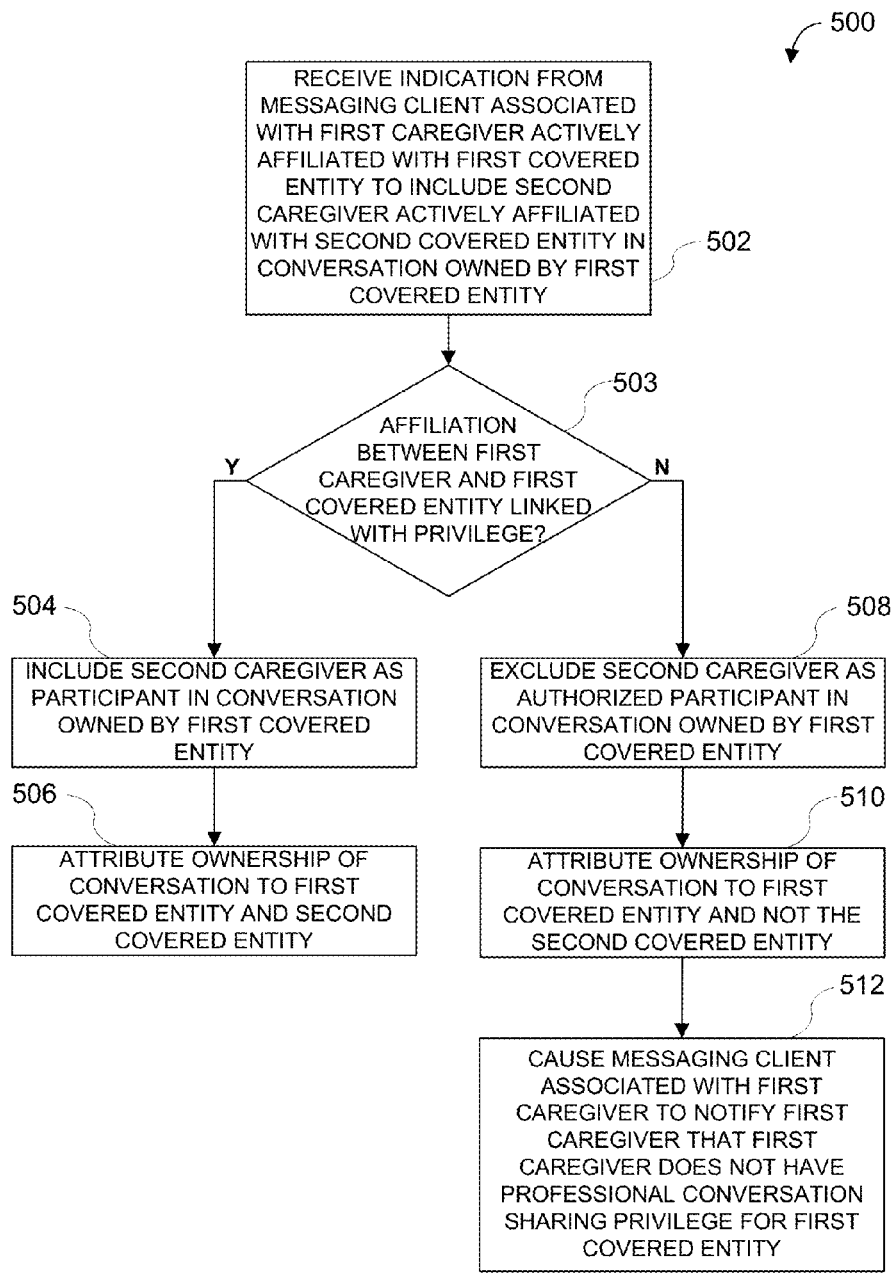
FIG. 5 is a flow diagram illustrating a process for sharing a conversation according to various embodiments.

FIG. 5 is a flow diagram illustrating a process 500 for sharing a conversation according to various embodiments. Referring to FIGS. 1 and 5, in various embodiments, the process 500 can be performed by the messaging platform 120.

In various embodiments, the messaging platform 120 can be configured to receive an indication from a messaging client associated with a first caregiver actively affiliated with the first covered entity to include a second caregiver actively affiliated with a second covered entity in a conversation owned by the first covered entity (502). For example, Caregiver B, who is actively affiliated with Covered Entity A, may be engaged in a conversation that is owned by Covered Entity A. Caregiver B can use the first messaging client 150 to indicate to the messaging platform 120 to include Caregiver C in the conversation. Caregiver C, however, is actively affiliated with Covered Entity B and not Covered Entity A. Thus, in some embodiments, the indication from Caregiver B can include a selection of the Covered Entity B as a new covered entity. In response to the selection of the Covered Entity B, the messaging platform 120 can provide, via the first messaging client 150, one or more caregivers who are actively affiliated with Covered Entity B. Caregiver B can then select Caregiver C from the one or more caregivers actively affiliated with Covered Entity B.

Alternately, in other embodiments, the indication from Caregiver B can include a request to specifically include Caregiver C as a new caregiver in the conversation. For example, in some embodiments, Caregiver B can provide a unique communication enabling personal identifier (e.g., email address, mobile phone number) for Caregiver C.

In response to the indication from the first caregiver, the messaging platform 120 can determine whether the affiliation between the first caregiver and the first covered entity is linked with a privilege to share the conversation (503). For example, Caregiver A can have the requisite conversation sharing privilege with respect to Covered Entity A, which allows Caregiver A to share conversations owned by Covered Entity A in which Caregiver A is a participant.

If the messaging platform 120 determines that the affiliation between the first caregiver and the first covered entity is linked with the privilege to share the conversation (503—Y), then the messaging platform 120 can be configured to include the second caregiver in the conversation owned by the first covered entity (504). Furthermore, the messaging platform 120 can be configured to attribute ownership of the conversation to the first covered entity and the second covered entity (506). As such, more than one covered entities (e.g., both Covered Entity A and Covered Entity B) can have accountability in the event that health information disclosed within the conversation is breached.

In some embodiments, prior to including Caregiver C in the conversation, the messaging platform 120 can be configured to obtain a legally binding digital signature from Caregiver C. For example, the messaging platform 120 can be configured to request, via the third messaging client 170, confirmation that Caregiver C has received HIPAA training in accordance with HIPAA regulations, and agrees to comply with HIPAA regulations for transmission and access to message data that is exchanged via the messaging platform 120. The messaging platform 120 can further obtain confirmation that Caregiver C is engaged in the direct care of a patient that is the subject of the shared patient-centered conversation.

In some embodiments, the messaging platform 120 can be configured to receive an indication from a messaging client associated with a first caregiver actively affiliated with a first covered entity to include a second caregiver D (not shown), who is not yet a user of the messaging platform 120. For example, in some embodiments, Caregiver B can provide a unique communication enabling personal identifier such as an email address or mobile phone number for Caregiver D to the messaging platform 120. The messaging platform 120 can be configured to make use of the unique communication enabling personal identifier to transmit an invitation to Caregiver D to become a user of the messaging platform 120. In some embodiments, prior to including Caregiver D in the conversation, the messaging platform 120 can be configured to obtain a legally binding digital signature from Caregiver D as described above.

On the other hand, the messaging platform 120 can determine that the affiliation between the first caregiver and the first covered entity is not linked with the privilege to share the conversation (503—N). For example, Caregiver A can have conversation sharing privilege with respect to Covered Entity B but not Covered Entity A. As such, the messaging platform 120 can be configured to exclude the second caregiver as an authorized participant in the conversation owned by the first covered entity (508).

In various embodiments, the messaging platform 120 can be configured to attribute ownership of the conversation to the first covered entity and not the second covered entity (510). Additionally, in some embodiments, the messaging platform 120 can cause a messaging client associated with the first caregiver to notify the first caregiver that the first caregiver does not have conversation sharing privilege for the first covered entity (512).

HIPAA-Compliant Ownership Transfer

In various embodiments, the messaging platform 120 can be configured to transfer ownership of a conversation from one covered entity to another. For instance, a patient may be transferred from one facility (e.g., hospital) to another facility (e.g., rehabilitation center). Thus, a patient-centered conversation can initially include caregivers having active affiliations with both Covered Entity A and Covered Entity B. For example, Caregiver A, Caregiver B, and Caregiver C can all be engaged in a patient-centered conversation that is initially owned by both Covered Entity A and Covered Entity B.

As the patient's care is gradually transferred from Covered Entity A to Covered Entity B, the patient-centered conversation can eventually include only caregivers who are actively affiliated with Covered Entity B (e.g., Caregiver A and Caregiver C). For example, Caregiver A and/or Caregiver B can have the requisite conversation transfer privilege with respect to Covered Entity A. The Caregiver A or Caregiver B can transfer ownership of the conversation from Covered Entity A to Covered Entity B. In response to this transfer of ownership, the messaging platform 120 can remove caregivers who are actively affiliated with Covered Entity A but not Covered Entity B as participants from the conversation. As a result, Caregiver B will no longer be able to participate in and access the conversation.

Figure 6:
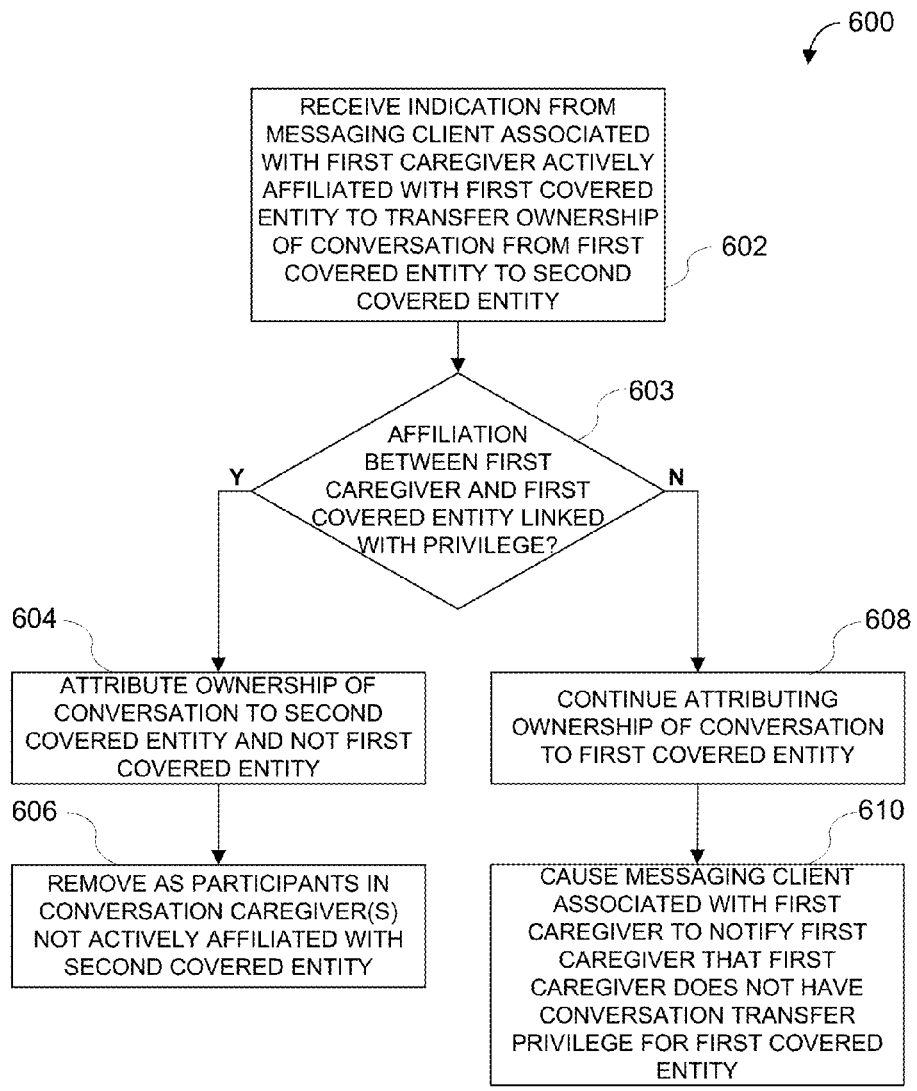
FIG. 6 is a flow diagram illustrating a process for transferring a conversation according to various embodiments.

FIG. 6 is a flow diagram illustrating a process 600 for transferring a conversation according to various embodiments. Referring to FIGS. 1 and 6, in various embodiments, the process 600 can be performed by the messaging platform 120.

In various embodiments, the messaging platform 120 can be configured to receive an indication from a messaging client associated with a first caregiver actively affiliated with a first covered entity to transfer ownership of a conversation from the first covered entity to a second covered entity (602). According to one exemplary embodiment, the messaging platform 120 can be configured to allow a caregiver to transfer ownership of a conversation whether or not the caregiver is a participant in the conversation. Alternately, the messaging platform can be configured to allow caregivers who are participants in a conversation to transfer ownership of the conversation.

In response to receiving the indication, the messaging platform 120 can be configured to determine whether the affiliation between the first caregiver and the first covered entity is linked with a privilege to transfer the conversation (603).

The messaging platform 120 can determine that the affiliation between the first caregiver and the first covered entity is linked with the privilege to transfer the conversation (603—Y). As such, the messaging platform 120 can be configured to attribute ownership of the conversation to the second covered entity and not the first covered entity (604). Transferring ownership of a conversation from one covered entity from another also transfers accountability from one covered entity to anther in the event that health information disclosed within the conversation is breached. For example, Covered Entity B instead of Covered Entity A can be held responsible for breaches of any PHI or EPHI contained within the conversation.

In addition, the messaging platform 120 can be configured to remove as participants in the conversation one or more caregivers who are not actively affiliated with the second covered entity (606). For example, Caregiver B is actively affiliated with only Covered Entity A. Thus, once the ownership of the conversation is transferred from Covered Entity A to Covered Entity B, the messaging platform 120 can be configured to remove Caregiver B as a participant from the conversation. Consequently, Caregiver B can no longer participate in or access the conversation.

Alternately, the messaging platform 120 can determine that the affiliation between the first caregiver and the first covered entity is not linked with the privilege to transfer the conversation (603—N). Accordingly, the messaging platform 120 can be configured to continue attributing the ownership of the conversation to the first covered entity (608). Moreover, the messaging platform 120 can be configured to cause a messaging client associated with the first caregiver to notify the first caregiver that the first caregiver does not have conversation transfer privilege for the first covered entity (610).

Patient-Covered Entity Associations

According to one exemplary embodiment, the messaging platform 120 can be configured to maintain a patient list that includes identification attributes including, for example, but not limited to, patient name, birthdate, contact information, and social security number. In various embodiments, the messaging platform 120 can be configured to maintain associations between a patient and one or more covered entities. For example, a patient can be associated with Covered Entity A and/or Covered Entity B.

In various embodiments, the affiliation between a covered entity and a caregiver can be linked with a privilege to link a patient in the patient list to a conversation owned by one or more covered entities. For example, Caregiver A can have patient linking privilege with respect to Covered Entity A and/or Covered Entity B.

In some embodiments, ownership of a patient-centered conversation regarding a specific patient can be restricted to the one or more covered entities that are associated with the patient. Thus, in various embodiments, in response to an indication from Caregiver A to link a conversation owned by Covered Entity A to a patient, the messaging platform 120 can be configured to determine whether the patient is associated with Covered Entity A.

Caregiver-Covered Entity Affiliations and Privileges

In various embodiments, the messaging platform 120 can be configured to update, track, and store affiliations between caregivers and covered entities. To ensure compliance with HIPAA mandates, the messaging platform 120 can be configured to restrict participation in and access to conversations owned by a covered entity to caregivers having active affiliations with the covered entity.

For example, while Caregiver A and Caregiver B are both actively affiliated with Covered Entity A, both Caregiver A and Caregiver B can be engaged in a conversation. The conversation can be a patient-centered conversation or a professional conversation that does not relate to any specific patient. In various embodiments, the messaging platform 120 can be configured to attribute ownership of the conversation between Caregiver A and Caregiver B to Covered Entity A.

In various embodiments, the affiliation between Caregiver A and Covered Entity A can be suspended temporarily or be terminated permanently. Consequently, Caregiver A is no longer actively affiliated with Covered Entity A. As such, the messaging platform 120 can be configured to remove Caregiver A as a participant in the conversation between Caregiver A and Caregiver B. Moreover, the messaging platform 120 can be configured to prohibit Caregiver A from accessing the conversation. In addition, when another caregiver who is actively affiliated with Covered Entity A (e.g., Caregiver B) initiates a patient-centered conversation owned by Covered Entity A, the messaging platform 120 can be configured to not identify Caregiver A as an authorized participant in the conversation.

In various embodiments, the affiliation between a caregiver and a covered entity can be linked with a privilege to administrate affiliations. For example, the affiliation between Caregiver A and Covered Entity A can be linked with an affiliation administrator privilege. According to one exemplary embodiment, a caregiver having affiliation administrator privilege for a covered entity is able add, activate, or reactivate an affiliation between another caregiver and the covered entity temporarily, permanently, and/or on a probationary basis. Alternately or in addition, the caregiver is able to deactivate or remove an affiliation between another caregiver and the covered entity temporary, permanently, and/or on a probationary basis.

Figures 7A, 7B:
FIG. 7A illustrates a screen display according to various embodiments.
FIG. 7B illustrates a screen display according to various embodiments.

FIG. 7A illustrates a screen display 700 according to various embodiments. Referring to FIGS. 1 and 7A, the screen display 700 can be part of the graphic user interface (GUI) provided by a messaging client (e.g., the first messaging client 150). As shown in FIG. 7A, the screen display 700 can show one or more conversations that a caregiver is engaged in. In one exemplary embodiment, the messaging client can be configured to display list enumerating the topic of each conversation. For example, Caregiver A can be engaged in multiple conversations including, for example, but not limited to, a patient-centered conversation regarding "Patient-John Doe."

FIG. 7B illustrates a screen display 750 according to various embodiments. Referring to FIGS. 1 and 7B, the screen display 750 can also be a part of the GUI provided by the messaging client (e.g., the first messaging client 150). As shown in FIG. 7B, the messaging client can be configured to display a specific conversation, including messages (e.g., text, photographs) that have been exchanged during the course of the conversation. For example, as shown in FIG. 7B, a caregiver is engaged in a patient-centered conversation regarding "Patient—James Hafner."

Figure 8:
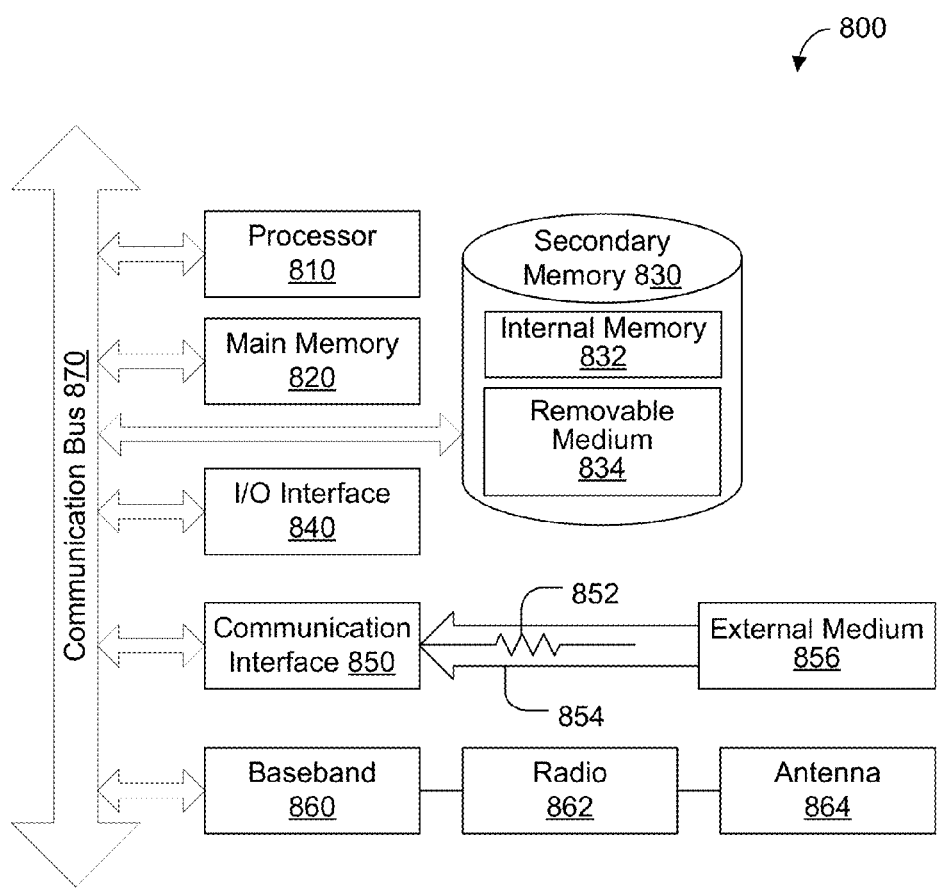
FIG. 8 is a block diagram illustrating a device according to various embodiments.

FIG. 8 illustrates a device 800 that is suitable for use in some embodiments of the systems and methods described herein. In some embodiments, the device 800 can be used to implement any of Devices 131-133 described with respect to FIGS. 1 and 2. In various embodiments, the device 800 can be used as is or in conjunction with one or more of the mechanisms or processes described above, and can represent components of server(s), user system(s), and/or other devices described herein. The device 800 can be a server or any conventional personal computer, or any other processor-enabled device that is capable of wired or wireless data communication. Other computer systems and/or architectures can be also used, as will be clear to those skilled in the art.

The device 800 preferably includes one or more processors, such as a processor 810. Additional processors can be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors can be discrete processors or can be integrated with the processor 810. Examples of processors which can be used with the device 800 include, without limitation, the Pentium® processor, Core i7® processor, and Xeon® processor, all of which are available from Intel Corporation of Santa Clara, Calif.

The processor 810 is preferably connected to a communication bus 870. The communication bus 870 can include a data channel for facilitating information transfer between storage and other peripheral components of the device 800. The communication bus 870 further can provide a set of signals used for communication with the processor 810, including a data bus, address bus, and control bus (not shown). The communication bus 870 can comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

The device 800 preferably includes a main memory 820 and can also include a secondary memory 830. The main memory 820 provides storage of instructions and data for programs executing on the processor 810, such as one or more of the functions and/or modules discussed above. It should be understood that programs stored in the memory and executed by the processor 810 can be written and/or compiled according to any suitable language, including without limitation C/C++, Java, JavaScript, Pearl, Visual Basic, .NET, and the like. The main memory 820 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 830 can optionally include an internal memory 832 and/or a removable storage medium 430, for example a floppy disk drive, a magnetic tape drive, a compact disc (CD) drive, a digital versatile disc (DVD) drive, other optical drive, a flash memory drive, etc. The removable storage medium 430 is read from and/or written to in a well-known manner. The removable storage medium 430 can be, for example, a floppy disk, magnetic tape, CD, DVD, SD card, etc.

The removable storage medium 430 can be a non-transitory computer-readable medium having stored thereon computer executable code (i.e., software) and/or data (e.g., for implementing at least a portion of the subject matter described herein). The computer software or data stored on the removable storage medium 430 is read into the device 800 for execution by the processor 810.

In alternative embodiments, the secondary memory 830 can include other similar means for allowing computer programs or other data or instructions to be loaded into the device 800. Such means can include, for example, an external storage medium 445 and an interface 440. Examples of the external storage medium 445 can include, for example, but not limited to, an external hard disk drive or an external optical drive, or and external magneto-optical drive.

Other examples of the secondary memory 830 can include semiconductor-based memory such as programmable read-only memory (PROM), erasable programmable read-only memory (EPROM), electrically erasable read-only memory (EEPROM), or flash memory (block oriented memory similar to EEPROM). Also included are a removable storage media 430 and a communication interface 850, which allow software and data to be transferred from an external medium 856 to the device 800.

The device 800 can include a communication interface 850. The communication interface 850 allows software and data to be transferred between the device 800 and various external devices (e.g. printers), networks, or information sources. For example, computer software or executable code can be transferred to the device 800 from a network server via the communication interface 850. Examples of the communication interface 850 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 firewire, or any other device capable of interfacing the device 800 with a network or another computing device.

The communication interface 850 preferably implements industry promulgated protocol standards including, for example, but not limited to Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but can also implement customized or non-standard interface protocols as well.

Software and data transferred via Communication Interface 440 are generally in the form of electrical communication signals 852. The electrical communication signals 852 are preferably provided to the communication interface 850 via a communication channel 854. In one embodiment, the communication channel 854 can be a wired or wireless network, or any variety of other communication links. The communication channel 854 carries the electrical communication signals 852 and can be implemented using a variety of wired or wireless communication means including, for example, but not limited to, wire or cable, fiber optics, conventional phone line, cellular phone link, wireless data communication link, radio frequency ("RF") link, or infrared link, just to name a few.

Computer executable code (i.e., computer programs or software) is stored in the main memory 820 and/or the secondary memory 830. Computer programs can also be received via the communication interface 850 and stored in the main memory 820 and/or the secondary memory 830. Such computer programs, when executed, enable the device 800 to perform the various functions, such as those described herein.

In this description, the term "computer readable medium" is used to refer to any non-transitory computer readable storage media used to provide computer executable code (e.g., software and computer programs) to the device 800. Examples of these media include the main memory 820, the secondary memory 830 (including the internal memory 832, the removable medium 834, and the external storage medium 445), and any peripheral device communicatively coupled with the communication interface 850 (including a network information server or other network device). These non-transitory computer readable mediums are means for providing executable code, programming instructions, and software to the device 800.

In an embodiment that is implemented using software, the software can be stored on a computer readable medium and loaded into the device 800 by way of the removable medium 834, the I/O interface 840, or the communication interface 850. In such an embodiment, the software is loaded into the device 800 in the form of the electrical communication signals 852. The software, when executed by the processor 810, preferably causes the processor 810 to perform the inventive features and functions previously described herein.

In an embodiment, the I/O interface 840 provides an interface between one or more components of the device 800 and one or more input and/or output devices. Example input devices include, without limitation, keyboards, touch screens or other touch-sensitive devices, biometric sensing devices, computer mice, trackballs, pen-based pointing devices, camera, microphone, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The device 800 also includes optional wireless communication components that facilitate wireless communication over a voice and over a data network. The wireless communication components can comprise an antenna system 864, a radio system 862, a baseband system 860, or any combination thereof. In the device 800, radio frequency (RF) signals are transmitted and received over the air by the antenna system 864 under the management of the radio system 862.

In one embodiment, the antenna system 864 can comprise one or more antennae and one or more multiplexors (not shown) that perform a switching function to provide the antenna system 864 with transmit and receive signal paths. In the receive path, received RF signals can be coupled from a multiplexor to a low noise amplifier (not shown) that amplifies the received RF signal and sends the amplified signal to the radio system 862.

In alternative embodiments, the radio system 862 can comprise one or more radios that are configured to communicate over various frequencies. In one embodiment, the radio system 862 can combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 862 to the baseband system 860.

If the received signal contains audio information, the baseband system 860 decodes the signal and converts it to an analog signal. Then the signal is amplified and sent to a speaker. The baseband system 860 also receives analog audio signals from a microphone. These analog audio signals are converted to digital signals and encoded by the baseband system 860. The baseband system 860 also codes the digital signals for transmission and generates a baseband transmit audio signal that is routed to the modulator portion of the radio system 862. The modulator mixes the baseband transmit audio signal with an RF carrier signal generating an RF transmit signal that is routed to the antenna system and can pass through a power amplifier (not shown). The power amplifier amplifies the RF transmit signal and routes it to the antenna system 864 where the signal is switched to the antenna port for transmission.

The baseband system 860 is also communicatively coupled with the processor 810. The processor 810 has access to the main memory 820 and the secondary memory 830. The processor 810 is preferably configured to execute instructions (i.e., computer programs or software) that can be stored in the main memory 820 or the secondary memory 830. Computer programs can also be received from the baseband processor 460 and stored in the main memory 820 or in the secondary memory 830, or executed upon receipt. Such computer programs, when executed, enable the device 800 to perform the various functions, such as those described herein. For example, the main memory 820 and the secondary memory 830 can each include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

In situations in which the systems discussed here collect personal information about users, or can make use of personal information, the users can be provided with an opportunity to control whether programs or features collect user information (e.g., information about a user's social network, social actions or activities, profession, a user's preferences, or a user's current location), or to control whether and/or how to receive content from the content server that can be more relevant to the user. In addition, certain data can be treated in one or more ways before it is stored or used, so that personally identifiable information is removed. For example, a user's identity can be treated so that no personally identifiable information can be determined for the user, or a user's geographic location can be generalized where location information is obtained (such as to a city, ZIP code, or state level), so that a particular location of a user cannot be determined. Thus, the user can have control over how information is collected about the user and used by a content server.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

Although a few example implementations have been shown and described, these example implementations are provided to convey the subject matter described herein to people who are familiar with this field. It should be understood that the subject matter described herein may be implemented in various forms without being limited to the described example implementations. The subject matter described herein can be practiced without those specifically defined or described matters or with other or different elements or matters not described. It will be appreciated by those familiar with this field that changes can be made in these example implementations without departing from the subject matter described herein as defined in the appended claims and their equivalents.

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed:
1. A system, comprising:
 a hardware processor;
 a database configured to store affiliation information between a plurality of caregivers and a plurality of covered entities, message data that includes ad hoc and unstructured electronic patient health information and that is associated with one or more ad hoc conversations, ownership data indicating for each conversation a covered entity of the plurality of covered entities that is assigned ownership of the message data, and affiliation information for each of the plurality of covered entities;
 an executable software module that, when executed by the at least one hardware processor, is configured to:

receive an indication to initiate a conversation from a messaging client associated with a first caregiver of the plurality of caregivers actively affiliated with a first covered entity of the plurality of covered entities and a second covered entity of the plurality of covered entities;

identify a second caregiver of the plurality of caregivers actively affiliated with the first covered entity and a third caregiver of the plurality of caregivers actively affiliated with the second covered entity as authorized participants in the conversation based on the affiliation information;

receive an indication from the messaging client associated with the first caregiver to include at least one of the second caregiver and the third caregiver in the conversation;

determine a number of common covered entities having active affiliations with every participant in the conversation;

in response to a determination that the number of common covered entities is greater than one:
select at least one common covered entity from the first and second covered entities; and
attribute ownership of the conversation to the selected covered entity.

2. The system as recited in claim 1, wherein the executable software module is further configured to exclude one or more caregivers not actively affiliated with the selected covered entity as authorized participants in the conversation.

3. The system as recited in claim 1, wherein the executable software module is configured to select the common covered entity based on input from at least one of the following: the first caregiver, the second caregiver, and a fourth caregiver of the plurality of caregivers actively affiliated with one of the common covered entities.

4. The system as recited in claim 1, wherein the executable software module is further configured to:
in response to a determination that the number of common covered entities is not greater than one:
attribute ownership of the conversation to the common covered entity;
associate data corresponding to the conversation with the common covered entity; and
store, in the database, the data corresponding to the conversation, and the association between the data and the covered entity.

5. The system as recited in claim 1, wherein the executable software module is further configured to:
receive an indication from the messaging client associated with the first caregiver to link the conversation with a patient;
determine whether the affiliation between the first caregiver and the selected covered entity is linked with a patient linking privilege;
in response to a determination that the affiliation between the first caregiver and the selected covered entity is linked with a patient linking privilege, determine whether the patient is associated with the selected covered entity; and
in response to a determination that the patient is associated with the selected covered entity, link the patient to the conversation owned by the selected covered entity.

6. The system as recited in claim 5, wherein the executable software module is configured to:
in response to a determination that the affiliation between the first caregiver and the selected covered entity is not linked with a patient linking privilege, cause the messaging client associated with the first caregiver to notify the first caregiver that the first caregiver does not have the privilege to link the patient to the conversation.

7. The system as recited in claim 5, wherein the executable software module is configured to:
in response to a determination that the patient is not associated with the selected covered entity, cause the messaging client associated with the first caregiver to notify the first caregiver that a patient not associated with the selected covered entity cannot be linked to the conversation owned by the selected covered entity.

8. The system as recited in claim 5, wherein the conversation comprises a patient-centered conversation relating to the patient.

9. The system as recited in claim 1, wherein the executable software module is further configured to cause the messaging client associated with the first caregiver to display one or more caregivers who are identified as authorized participants in the conversation.

10. The system as recited in claim 1, wherein the executable software module is further configured to:
detect that an affiliation between the first caregiver and the selected covered entity has been deactivated;
exclude the first caregiver as an authorized participant in the conversation; and
prohibit the first caregiver from accessing message data comprising the conversation.

11. A method, comprising:
Storing, in a database, affiliation information between a plurality of caregivers and a plurality of covered entities, message data that includes ad hoc and unstructured electronic patient health information and that is associated with one or more ad hoc conversations, ownership data indicating for each conversation a covered entity of the plurality of covered entities that is assigned ownership of the message data, and affiliation information for each of the plurality of covered entities
receiving an indication to initiate a conversation from a messaging client associated with a first caregiver of the plurality of caregivers actively affiliated with a first covered entity of the plurality of covered entities and a second covered entity of the plurality of covered entities;
identifying, using a hardware processor, a second caregiver of the plurality of caregivers actively affiliated with the first covered entity and a third caregiver of the plurality of caregivers actively affiliated with the second covered entity as authorized participants in the conversation based on the affiliation information;
receiving an indication from the messaging client associated with the first caregiver to include at least one of the second caregiver and the third caregiver in the conversation;
determining a number of common covered entities having active affiliations with every participant in the conversation;
in response to a determination that the number of common covered entities is greater than one:
selecting at least one common covered entity from the first and second covered entities; and
attributing ownership of the conversation to the selected covered entity.

12. The method as recited in claim 11, further comprising excluding one or more caregivers not actively affiliated with the selected covered entity as authorized participants in the conversation.

13. The method as recited in claim 11, further comprising selecting the common covered entity based on input from at least one of the following: the first caregiver, the second caregiver, and a fourth caregiver of the plurality of caregivers actively affiliated with one of the common covered entities.

14. The method as recited in claim 11, further comprising:
in response to a determination that the number of common covered entities is not greater than one:
attributing ownership of the conversation to the common covered entity;
associating data corresponding to the conversation with the common covered entity; and
storing the data corresponding to the conversation, and the association between the data and the covered entity.

15. The method as recited in claim 11, further comprising:
receiving an indication from the messaging client associated with the first caregiver to link the conversation with a patient;
determining whether the affiliation between the first caregiver and the selected covered entity is linked with a patient linking privilege;
in response to a determination that the affiliation between the first caregiver and the selected covered entity is linked with a patient linking privilege, determining whether the patient is associated with the selected covered entity; and
in response to a determination that the patient is associated with the selected covered entity, linking the patient to the conversation owned by the selected covered entity.

16. The method as recited in claim 15, further comprising:
in response to a determination that the affiliation between the first caregiver and the selected covered entity is not linked with a patient linking privilege, causing the messaging client associated with the first caregiver to notify the first caregiver that the first caregiver does not have the privilege to link the patient to the conversation.

17. The method as recited in claim 15, further comprising:
in response to a determination that the patient is not associated with the selected covered entity, causing the messaging client associated with the first caregiver to notify the first caregiver that a patient not associated with the selected covered entity cannot be linked to the conversation owned by the selected covered entity.

18. The method as recited in claim 15, wherein the conversation comprises a patient-centered conversation relating to the patient.

19. The method as recited in claim 11, further comprising causing the messaging client associated with the first caregiver to display one or more caregivers who are identified as authorized participants in the conversation.

20. The method as recited in claim 11, further comprising:
detecting that an affiliation between the first caregiver and the selected covered entity has been deactivated;
excluding the first caregiver as an authorized participant in the conversation; and
prohibiting the first caregiver from accessing message data comprising the conversation.

* * * * *